United States Patent
Tan et al.

(10) Patent No.: US 8,942,787 B2
(45) Date of Patent: Jan. 27, 2015

(54) SOFT FIELD TOMOGRAPHY SYSTEM AND METHOD

(75) Inventors: Wei Tan, Shanghai (CN); Alexander Seth Ross, Albany, NY (US); Veera Venkata Lakshmi Rajesh Langoju, Bangalore (IN); Ran Niu, Shanghai (CN); Zhilin Wu, Shanghai (CN); Weihua Gao, Shanghai (CN)

(73) Assignee: General Electric Company, Schenectady, NY (US)

( * ) Notice: Subject to any disclaimer, the term of this patent is extended or adjusted under 35 U.S.C. 154(b) by 69 days.

(21) Appl. No.: 13/316,514

(22) Filed: Dec. 11, 2011

(65) Prior Publication Data
US 2012/0172719 A1 Jul. 5, 2012

(30) Foreign Application Priority Data

Dec. 29, 2010 (CN) .......................... 2010 1 0612087

(51) Int. Cl.
*A61B 5/05* (2006.01)

(52) U.S. Cl.
USPC .......................................... 600/425; 600/407

(58) Field of Classification Search
USPC ................................................ 600/425, 407
See application file for complete search history.

(56) References Cited

U.S. PATENT DOCUMENTS

| | | | |
|---|---|---|---|
| 5,841,288 A | 11/1998 | Meaney et al. | |
| 6,387,671 B1 | 5/2002 | Rubinsky et al. | |
| 7,435,226 B2 | 10/2008 | Suarez | |
| 2008/0246489 A1 | 10/2008 | Coster et al. | |
| 2008/0252304 A1 | 10/2008 | Woo et al. | |

FOREIGN PATENT DOCUMENTS

| | | |
|---|---|---|
| EP | 2310840 A1 | 4/2011 |
| WO | 2007109678 A2 | 9/2007 |
| WO | 2011100343 A2 | 8/2011 |

OTHER PUBLICATIONS

Image Reconstruction Algorithms for Soft-Field Tomography by Nicholas Polydorides Manchester, United Kingdom Sep. 2002.*
Explicit Mesh Deformation Using Inverse Distance Weighting Interpolation by Jeroen A.S. Witteveen 19th AIAA Computational Fluid Dynamics Jun. 22-25, 2009.*
Inverse distance weighting From Wikipedia, accessed Sep. 18, 2013, published Feb. 15, 2005.*

(Continued)

*Primary Examiner* — Long V. Le
*Assistant Examiner* — Michael Kellogg
(74) *Attorney, Agent, or Firm* — GE Global Patent Operation; Marc A. Vivenzio (57) ABSTRACT

An iteration method for computing a distribution of one or more properties within an object comprises defining a first mesh of the object, applying an excitation to the object, computing a response of the object to the applied excitation, obtaining a reference response of the object corresponding to the applied excitation, computing a distribution of one or more properties of the object, and updating at least a subset of the nodes of the first mesh to form an updated mesh of the object. The distribution of one or more properties of the object is computed using the computed response, the reference response, and the first mesh. The first mesh includes a plurality of nodes and elements. A connectivity relationship of the subset of the nodes in the updated mesh remains the same as in the first mesh.

17 Claims, 6 Drawing Sheets

(56) References Cited

OTHER PUBLICATIONS

An r-Adaptive Finite Element Method Based upon Moving Mesh PDEs by Cao et al. Journal of Computational Physics 149, 221-244 (1999).*

EIDORS: Electrical Impedance Tomography and Diffuse Optical Tomography Reconstruction Software http://eidors3d.sourceforge.net/, accessed Sep. 17, 2013, published (latest code version) 2006.*

Search Report from corresponding GB Application No. 1121850.0 Apr. 30, 2012.

* cited by examiner

SOFT FIELD TOMOGRAPHY SYSTEM AND METHOD

BACKGROUND

Embodiments of the invention relate generally to measurement instruments, and more particularly, to a system and a method for measurement or imaging.

Soft field tomography (SFT) is a technique that measures or images the internal structure of an object, such as a region of a human body by computing a distribution of one or more properties of the internal structure. SFT includes, but is not limited to, Electrical Impedance Tomography (EIT), Electrical Impedance Spectroscopy (EIS), Diffuse Optical Tomography (DOT), Microwave Tomography, Elastography, and Magnetic Induction Tomography (MIT). In the example of reconstructing properties of the human chest using EIT, electrical properties are different for air and body tissues. Moreover, the electrical properties of the body tissues also vary with time. Accordingly, a time-varying map of the electrical properties within the body region can be generated.

A typical SFT system for measuring or imaging distributed properties of an object comprises a plurality of sensing elements arranged on a peripheral surface of the object to be imaged. Excitations are applied to all or a subset of the sensing elements, and a measurement device measures the response of all or a subset of the sensing elements. The applied excitations and measured responses are processed to create a two-dimensional or three-dimensional property distribution of the object, which may be processed into one or more images. In the example of EIT, the sensing elements are electrodes that conduct electrical current. The excitations applied to the electrodes can be electrical current, and the measured response can be voltages. The property distribution of the internal structure to be determined can be a distribution of electrical impedance, electrical admittivity, electrical permittivity, or electrical conductivity.

One method for computation of the property distribution of the internal structure uses finite element modeling (FEM), which discretizes the space inside the object into finite elements. The properties on these elements are solved with an inverse solver, for example, based on a forward mapping of applied currents or voltages on the conductivity distribution to measured voltages or currents on the electrodes. A two-dimensional or three-dimensional image of the internal structure of the object may be obtained based on the computed property distribution.

The resolution of the image obtained using typical SFT systems is restricted by the number of independent measurements available, or in other words, by the number of sensing elements employed. Generally, the more solvable finite elements there are in the FEM analysis, the better the resolution of the obtained image will be. For a given number of sensing elements, the number of solvable variables is limited. One conventional method for improving the resolution of the measurement is to increase the number of sensing elements applied to the object. However, for a fixed excitation energy and system precision, the signal-to-noise ratio drops with the increase of the number of the sensing elements. Further, a large number of sensing elements make the system bulky and expensive.

There is a need in the art to provide a different SFT system and method with improved resolution at regions of interest without adding to the number of sensing elements applied to the object to be measured.

BRIEF DESCRIPTION

In accordance with one exemplary embodiment of the invention, an iteration method for computing a distribution of one or more properties within an object comprises defining a first mesh of the object, applying an excitation to the object, computing a response of the object to the applied, excitation, obtaining a reference response of the object corresponding to the applied excitation, computing a distribution of one or more properties of the object, and updating at least a subset of the nodes of the first mesh to form an updated mesh of the object. The distribution of one or more properties of the object is computed using the computed response, the reference response, and the first mesh. The first mesh includes a plurality of nodes and elements. A connectivity relationship of the subset of the nodes in the updated mesh remains the same as in the first mesh.

In accordance with another exemplary embodiment of the invention, a soft field tomography system comprises a plurality of sensing elements coupled to an object, an excitation driver coupled to the plurality of sensing elements for transmitting an excitation to the plurality of sensing elements, and a computing device coupled to the excitation driver. The computing device defines a first mesh of the object, the first mesh including a plurality of nodes and elements, computes a response of the object according to the applied excitation, obtains a reference response to the applied excitation, computes a distribution of one or more properties of the object using the computed response, the reference response and first mesh, identifies a region of interest according to the computed distribution of the one or more properties of the object, and updates at least a subset of the nodes in the first mesh to generate an updated mesh of the object. A connectivity relationship of the subset of the nodes in the updated mesh remains the same as in the first mesh.

In accordance with still another exemplary embodiment of the invention, a computer readable medium comprising non-transitory instructions which when executed performs the method of defining a first mesh of an object, the first mesh including a plurality of nodes and elements, applying an excitation to the object, computing a response of the object to the applied excitation, obtaining a reference response of the object corresponding to the applied excitation, computing a distribution of one or more properties of the object using the computed response, the reference response and the first mesh, and updating at least a subset of the nodes in the first mesh to form an updated mesh of the object. A connectivity relationship of the subset of the nodes in the updated mesh remains the same as in the first mesh.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments disclosed herein relate to a soft field tomography ("SFT") system and method for reconstructing and displaying an internal structure of an object by measuring a distribution of a property of the internal structure. As used herein, "SFT" refers to a method that generates the property distribution to be measured within the object under an influence of an excitation field such an electrical field, a magnetic field, an acoustic excitation, a mechanical excitation, a thermal field, or an optical field. In certain embodiments, each of the excitations, measurements and distributed properties may be real, imaginary, or complex. Examples of SFT include but are not limited to Electrical Impedance Tomography (EIT), Electrical Impedance Spectroscopy ("EIS"), Diffuse Optical Tomography (DOT), elastography, thermography, and Near InfraRed Spectroscopy (NIRS), Embodiments described hereinafter use EIT for imaging the internal structure of the object by measuring a distribution of electrical properties of the object. Embodiments of the invention can be also used with other SFT methods such as EIS, DOT and NIRS for example.

Embodiments of the invention may be described herein in terms of functional and/or block components and various processing steps. It should be appreciated that such block components may be realized by any number of hardware, software, and/or firmware components configured to perform the specific functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, embodiments of the present invention may be practiced in conjunction with any number of data transmission protocols. Moreover, the system described herein merely illustrates one exemplary embodiment.

Figure 1:
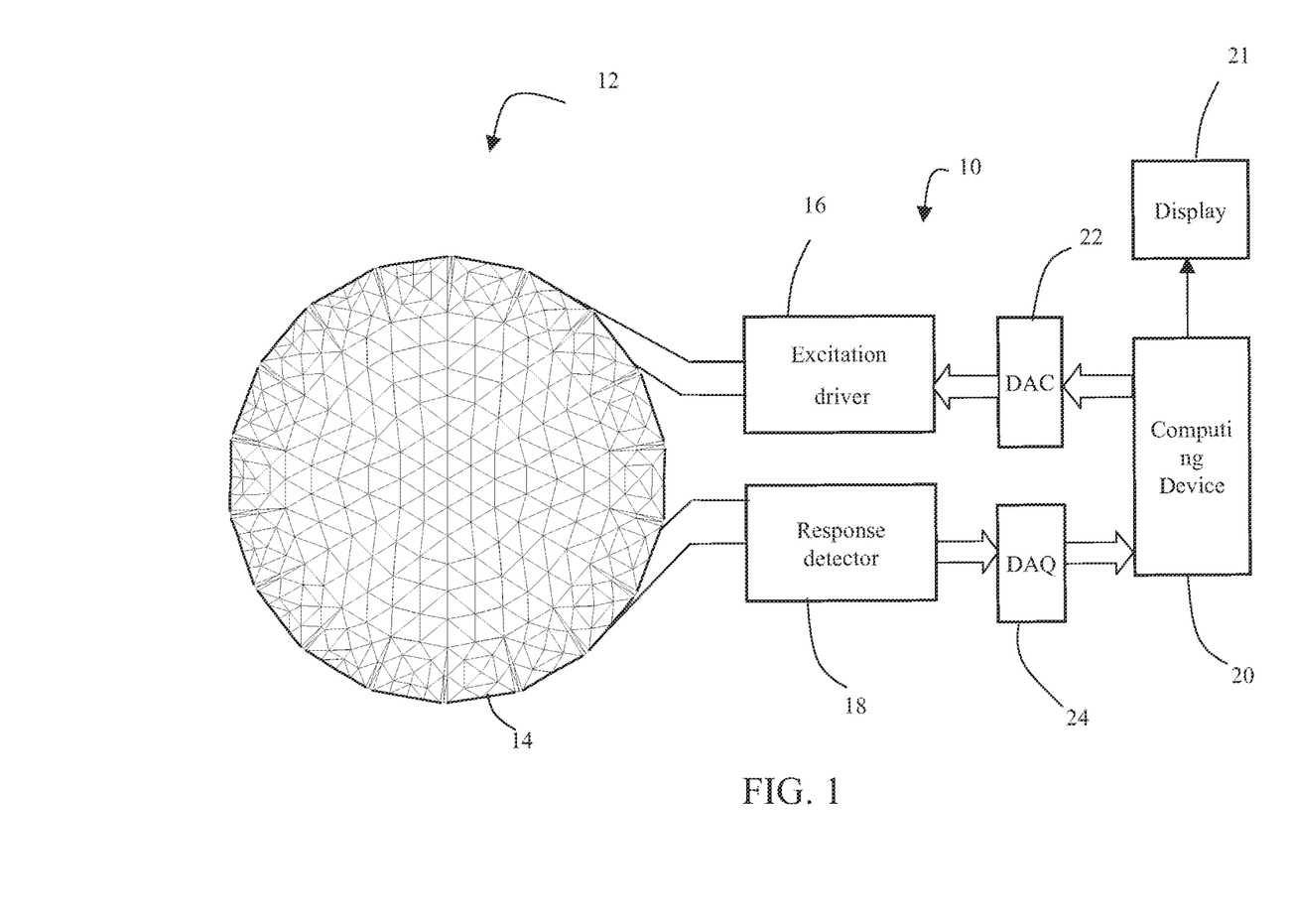
FIG. 1 is schematic view of a Soft field tomography (SFT) system for imaging an object according to one embodiment.

Referring to FIG. 1, an exemplary SFT system 10 for imaging an internal structure of an object 12 by measuring a distribution of the properties of the object 12 is illustrated. In the illustrated embodiment, the system 10 is an SFT system which comprises a plurality of sensing elements 14 coupled to the object 12, an excitation driver 16 and a response detector 18 electrically coupled to the sensing elements 14, and a computing device 20 electrically coupled to the excitation driver 16 and the response detector 18. In the illustrated embodiment of FIG. 1, the system 10 further comprises a display 21 to display an image of the object 12 generated by the system.

In the illustrated embodiment of FIG. 1, an excitation applied to the sensing elements 14 by the excitation driver 16 and a reference response obtained by the response detector 18 are both electrical signals such as an electrical current and an electrical potential. In other embodiments, the excitation by the excitation driver 16 may include one or more of electrical signals, optical signals, thermal sources, mechanical excitations, acoustic signals, and magnetic fields; and the reference response may include one or more of electrical signals, optical signals, thermal responses, mechanical responses, acoustic responses, and magnetic field responses. In the illustrated embodiment, the computing device 20 sends signals to the excitation driver 16 through a digital to analog converter (DAC) 22. In the illustrated embodiment, the computing device 20 receives data from the response detector 18 through a Data-Acquisition element (DAQ) 24. Each of the DAC and DAQ may be any device performing the function. In one embodiment, the excitation driver 16, the response detector 18, the DAC 22, the DAQ 24 and the computing device 20 are physically separate devices. In other embodiments, two or more of these elements may be physically integrated as one element.

The object 12 may represent a variety of structures or regions such as, but not limited to a human body region, a pipe or containment vessel, and a geologic region. Each of these objects 12 may contain or exhibit different properties including but not limited to electrical conductivities, impedances, admittivities, thermal properties, elasticity, optical absorbance, optical scattering, or acoustic reflection. In accordance with embodiments of the invention, images generated by the SFT system 10 illustrate conditions of the internal properties of the object. For example, the SFT system 10 can be used for generating images in a variety of applications including human imaging involving a mix of blood, air and tissue, pipeline imaging involving a mixed flow including oil and water, and underground imaging involving a mix of soils and liquids such as water and oil.

In the illustrated embodiment of FIG. 1, the sensing elements 14 are positioned on an outer periphery of the object 12. In alternative embodiments, all or a subset of the sensing elements 14 may comprise needles or rods at least partially inserted, extending into, or fully contained in the object 10. In the illustrated embodiment where the sensing elements 14 are positioned on the outer periphery, the sensing elements 14 may comprise any conductive material used for establishing a flow of electrical current between the object 12 and the SFT system 10. Exemplary material for the sensing elements may comprise metals or alloys such as copper, gold, platinum, steel, silver, and alloys thereof. Other exemplary materials for the sensing elements 14 may comprise non-metals that are electrically conductive, such as silicon-based materials used in connection with microcircuits. In one embodiment where the SFT system 10 is employed for imaging a human body region (e.g., the object 12), the sensing elements 14 comprise silver-silver chloride. In certain embodiments, the sensing elements 14 may be rod-shaped, flat plate-shaped, or needle-shaped structures. In certain embodiments, the sensing elements 14 may be used to deliver electrical current continuously or to deliver electrical current in pulses. In certain embodiments, the sensing elements 14 are electrically insulated from one another, in certain embodiments, the sensing elements 14 can be positioned in direct ohmic contact with the object 12 or be capacitively coupled to the object 12.

In certain embodiments, the excitation driver 16 applies an excitation to each of the sensing elements 14. In one embodiment, the excitation driver 16 comprises a current source (not shown) and a one-to-multichannel switch (not shown) for transmitting electrical currents to the plurality of sensing elements 14. In another embodiment, the excitation driver 16 comprises a plurality of current sources each for applying an electrical current to a corresponding sensing element 14. The excitation driver 16 may apply a direct current, an alternating current, or a combined direct and alternating current to each of the sensing elements 14. In one embodiment for imaging a human body region, the electrical current applied to the sensing elements 14 is between 0 to 0.1 mA at a frequency of 50 kHz. In one embodiment, the excitation driver 16 comprises at least one voltage source for applying a voltage to each of the sensing elements 14.

In certain embodiments, the response detector 18 measures a response signal on each of the sensing elements 14 in response to the excitation applied to the sensing elements 14. In one embodiment, the response detector 18 comprises a voltage sensor or a current sensor to measure a response voltage or a response current on the sensing elements 14 in response to the current or voltage applied by the excitation driver 16. In one embodiment, the response detector 18 further comprises a multi-channel analog-signal-conditioning-circuit that amplifies and/or filters the measured response voltage or current. In other embodiments, the computing device 20 comprises a signal conditioning circuit to amplify and/or filter the response voltage or response current received from the response detector 18. In one embodiment, the response detector 18 sends the measured data to the computing device 20 and/or the DAQ 24 in real-time. In other words, the response detector 18 sends the response voltage or current to the computing device 20 without any unnecessary delay except the time period for processing the data. In other embodiments, the response detector 18 communicates with the computing device 20 and/or the DAQ 24 at a determined time interval.

In certain embodiments, a method for generating an image of the internal structure of the object 12 includes the computing device 20 defining a first mesh of the object 12, and the first mesh includes a plurality of nodes and elements. The excitation driver 16 applies an excitation to the object 12, and the computing device 20 computes a response ("computed response") by the object 12 to the applied excitation. The computing device 20 obtains a reference response of the applied excitation, and computes a distribution of properties of the object 12 using the computed response, the reference response and the first mesh. The computing device 20 further updates at least a subset of the nodes in the first mesh to form an updated mesh. The connectivity relationship of the nodes in the updated mesh remains the same as in the first mesh. In certain embodiments, the excitation driver 16 applies an updated excitation to the object 12. The computing device 20 then computes an updated response to the updated excitation, and computes an updated distribution of properties using the updated computed response, the reference response, and the updated mesh.

Figure 2:
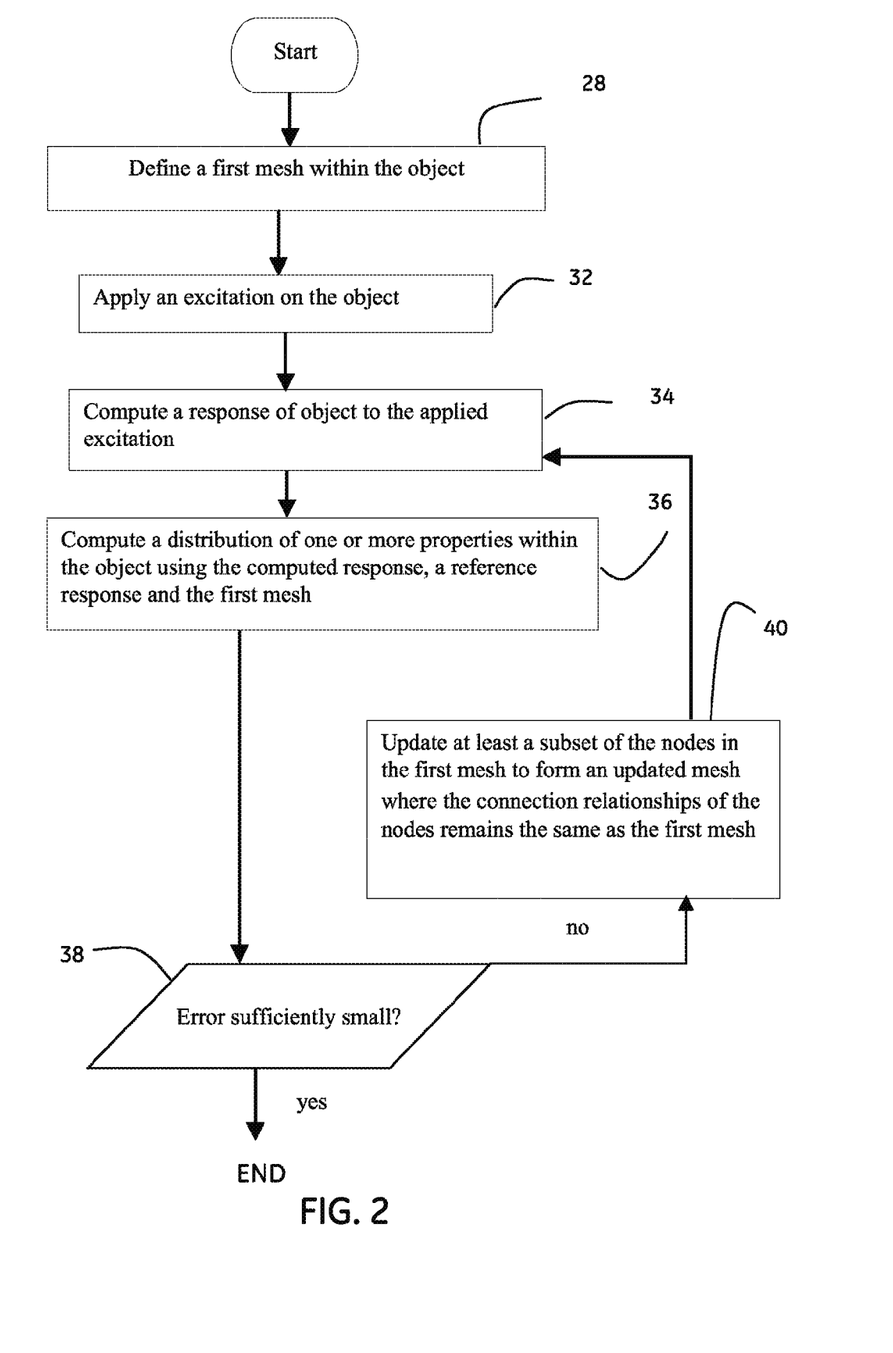
FIG. 2 is a flow chart of a SFT method of imaging the object according to one embodiment.

Referring to FIG. 2 in conjunction with FIG. 1, an exemplary SFT method which is an iterative method for generating an image of the internal structure of the object 12 according to one embodiment is shown. In one embodiment, the SFT method is a software processed by a computer such as the computing device 20. In another embodiment, the SFT method is performed by a plurality of hardware. The iterative method comprises the computing device 20 defining a first mesh of the object 12 at block 28. The excitation driver 1616 applies an excitation to the object 12 at block 32, and the computing device 20 computes a response of the object 12 to the applied excitation at block 34. The method continues at block 36, where the computing device 20 computes a distribution of one or more properties of the object 12 using the computed response and a reference response. At block 38, in the illustrated embodiment, the computing device 20 determines if the process ends or continues with a next iteration at block 40 according to a determined resolution requirement for example. In one embodiment, if an error between the computed distribution of properties and a computed distribution of properties of a previous iteration is smaller than a determined value, the process ends. Otherwise, the process continues at block 40, at which the computing device 20 updates at least a subset of the nodes in the first mesh to form an updated mesh. In certain embodiments, the number of nodes and connectivity relationships of the nodes in the updated mesh remains the same as the first mesh. In certain embodiments, the steps of blocks 28-40 repeat until the error determined at block 38 is sufficiently small.

In certain embodiments, at the start of the method, the computing device 20 defines a geometry of the object 12. In certain embodiments, the computing device 20 generates an assumption of the shape of the geometry for example, and generates an assumption on a distribution of the properties of the object 12. For example, if generating a three-dimensional image of the internal structure of the object 12, the computing device 20 may generate a geometry that is a three-dimensional space of the object 12 surrounded by the sensing elements 14. Similarly, if generating a two-dimensional image of a slice of the internal structure of the object 12, the computing device 20 may generate a geometry that is a two-dimensional area surrounded by at least parts of the sensing elements 14. In one embodiment, the computing device 20 generates an assumption that the internal structure of the object 12 has a uniformly distributed property. In one embodiment, the computing device 20 generates an assumption that the geometry of the object 12 has a symmetrical or analytically defined boundary.

Figure 3:
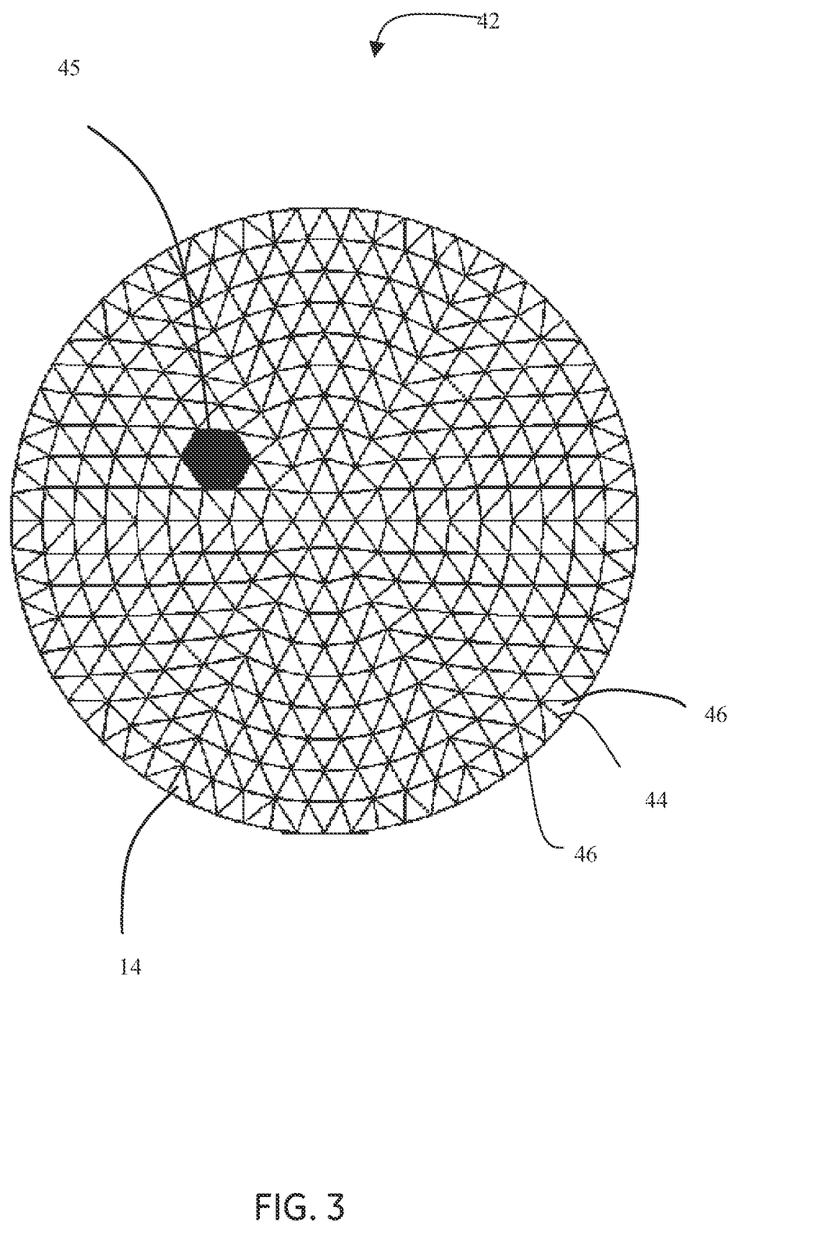
FIG. 3 illustrates a first mesh defined in the object during the SFT method of imaging the object according to one embodiment.

An exemplary first mesh 42 defined at block 28 is illustrated in FIG. 3. The illustrated first mesh 42 is a triangle mesh including a plurality of regular triangular elements 44 each defined by three nodes 46. The sensing elements 14 on the outer peripheral of the object 12 define a plurality of external boundaries of the first mesh 42, and each internal line between two nodes 46 defines an internal boundary of the corresponding element 44. In certain embodiments, the number of elements 44 matches the number of excitations applied to the geometry by the excitation driver 16 as discussed later. In the two-dimensional geometry embodiment, the first mesh 42 is a two-dimensional mesh and the elements 44 are in two-dimensions. In the three-dimensional geometry embodiment, the mesh 42 and the elements 44 in the first mesh are in three-dimensions, and the reconstruction obtained is a three-dimensional image of the internal structure of the object 12. In other embodiments, the mesh 42 can be any other mesh that supports FEM computation, such as a rectangular type mesh including a plurality of rectangular elements or a tetrahedral mesh including a plurality of tetrahedral elements. In certain embodiments, the mesh 42 can be generated with commercially available automatic meshing software.

Referring back to FIG. 2, at block 32, the excitation driver 16 applies an excitation on the geometry. In one embodiment, the excitation driver 16 applies an electrical current on the plurality of sensing elements 14. In another embodiment, the excitation is an electrical voltage applied to the sensing elements 14 by the excitation driver 16. In one embodiment, the excitation is a sinusoidal current or voltage with determined amplitudes and phases that optimizes signal to noise ratio. In one embodiment, the excitation is applied simultaneously to the plurality of sensing elements 14 in parallel or through the one-to-multichannel switch. In another embodiment, the excitation is applied to the plurality of sensing elements 14 sequentially. In certain embodiments, the excitation applied to each sensing elements may be the same or different. In certain embodiments, the excitation driver 16 applies at least two sets of current or voltage to each of the sensing elements 14 sequentially. Accordingly, the total number of excitations applied to the sensing elements will be a multiple of the number of the sensing elements 14 on the object 12.

At block 34, in the illustrated embodiment, the computing device 20 computes a response of the geometry of the object 12 to the applied excitation. In one embodiment, the computer device 20 computes the response using an analytical system of equations. In another embodiment, the computer device 20 establishes a relationship between the excitation applied to the geometry and the corresponding computed response using the first mesh. In still another embodiment, the computer device 20 establishes a relationship between the excitation applied to the geometry and the corresponding computed response using another mesh rather than the first mesh. In the illustrated electrical current excitation embodiment, the computed response or potential ($U_E$) at the sensing elements can be obtained according to equation 1 below:

$$[A] \begin{bmatrix} U \\ U_E \end{bmatrix} = \begin{bmatrix} 0 \\ I_d \end{bmatrix}, \quad \text{equation 1}$$

wherein "A" is a matrix that is determined by the distribution of conductivity of geometry of the object 12; "U" is a potential distribution of object 12 that can not be directly measured; "$U_E$" is the computed potential at the sensing elements 14; and "$I_d$" is the excitation or current applied on the sensing elements 14. Accordingly, for a given set of excitation or current ($I_d$) applied on the sensing elements 14, the response or electrical potential (U) induced in the object 12 and the response or potential ($U_E$) at the sensing elements can be computed by solving equation 1. In one embodiment, the computed response ($U_E$) comprises a plurality of computed potentials respectively on the corresponding sensing elements 14 in response to the applied electrical excitation or current, in one exemplary method of computing the response potential, the computing device 20 configures a finite element model (FEM) according to the first mesh 42 defined at block 30. Because it is assumed that there are no internal electrical sources in the geometry, the electrical field in the geometry can be described with the continuum form of Kirchoff's law (equation 2):

$$\nabla \cdot (\sigma \nabla u) = 0, \quad \text{equation 2}$$

wherein "∇" is the Laplace operator, "u" is the potential at a point in the mesh, "σ" is admittivity, and "∇·" is a divergence operator.

Conditions at the external boundaries of the geometry covered by the sensing elements 14 are mathematically governed by Gauss' Theorem (equation 3):

$$\int_{El} \cdot \sigma \frac{\partial u}{\partial \vec{r}} ds = \vec{I}, \quad \text{equation 3}$$

wherein "s" is a boundary surface of the external boundaries, "$\vec{r}$" is a vector normal to the boundary surface (s), and "I" is a current vector at all sensing elements 14. For the internal boundaries within the geometry, the condition is described as equation 4:

$$\sigma \frac{\partial u}{\partial \vec{r}} = 0. \quad \text{equation 4}$$

Accordingly, at block 34, the computing device 20 receives an estimated set of admittivities (σ), and computes the computed response ($U_E$) according to the applied excitation. With the finite element method, equations 2-4 are applied to each element 44 in the first mesh 42. Accordingly, the system matrix (A) in equation 1 includes the geometry of the object 12 and the estimated set of admittivities (σ) which can be obtained by solving equations 2-4.

In one embodiment, the computing device 20 assumes that the each of the elements 44 in the determined first mesh 42 have a uniform admittivity ($\sigma_i$) within the external boundaries. The potential distribution (U) within the external boundaries is a continuous function of location (x, y, z).

Figure 4:
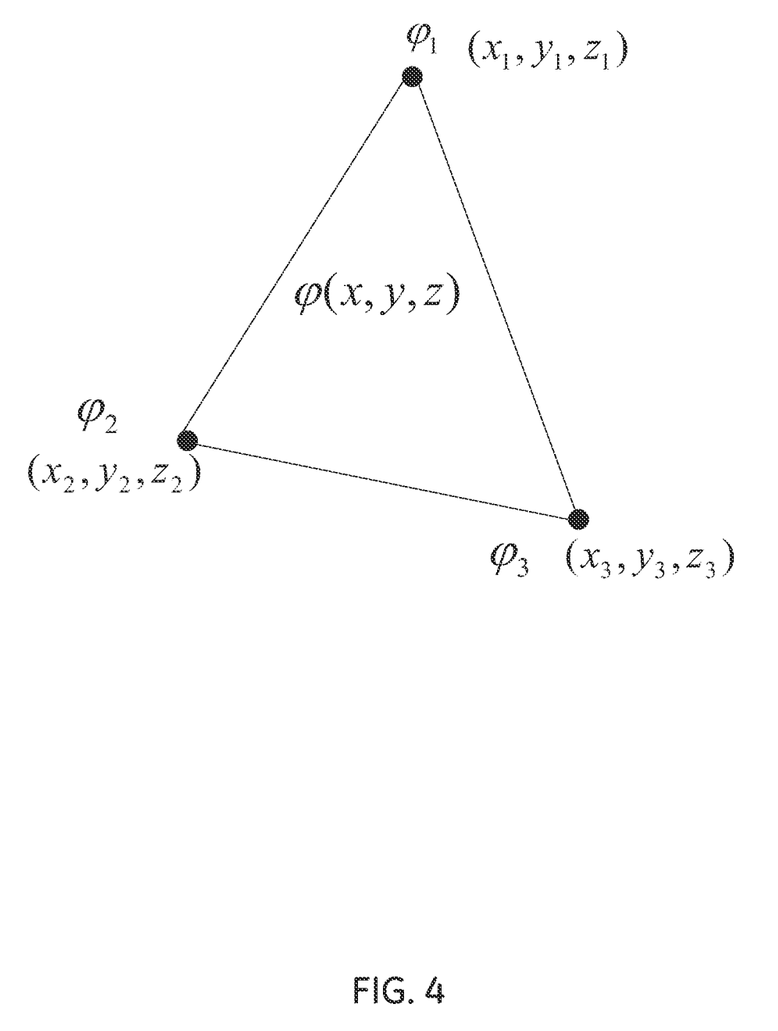
FIG. 4 illustrates three nodes of the first mesh which defines an element according to one embodiment.

In certain embodiments, the potential (U) within each element 44 is approximated as linear combinations of a set of basis functions, weighted with the potential ($u_{node\_i}$) at the nodes of each element. In certain embodiments, the computing device 20 computes a local matrix (Ae) on each element 44. In certain embodiments, the admittivity ($\sigma_i$) and the electric potential (u) interpolated with the set of basis functions are combined into the local matrix (Ae). The potential ($u_{node\_i}$) at each of the nodes forms a vector u=[u1 u2 u3]' for a two-dimensional triangle element, as shown in FIG. 4. The potential ($u_{node\_i}$) at each of the nodes in one element forms a vector u=[u1 u2 u3 u4]' for a three dimensional tetrahedral element (not shown). The applied excitation or current forms another vector (b). Accordingly, equations 2-4 can be simplified as a local system equation below for each element as equation 5:

$$Ae*u=b. \quad \text{equation 5}$$

In certain embodiments, the computing device 20 assembles the local matrices (Ae) into the system matrix (A) according to the interconnection of the elements 44, and the local system equation (equation 5) can be assembled to cover the whole geometry. The computed response ($U_E$) at the sensing elements 14 can then be obtained by equation 6:

$$[u_E] = U_E(\sigma, I) = J(\rho)I, \quad \text{equation 6}$$

wherein "I" is the applied current (excitation) in matrix format, "ρ" is impedivity which is the inverse of admittivity (σ), "U" is a potential function in matrix format, and "J" is the Jacobian matrix. The computed responses ($U_E$) are then obtained by solving equation 6.

With continued reference to FIG. 2, at block 36, the computing device 20 computes a distribution of one or more properties on the geometry using the computed response and a reference response. In one embodiment, the reference response is a measured response at the sensing elements 14 by the response detector 18. In other embodiments, the reference response can be an signal obtained by simulation or obtained from a reference database. In one embodiment, the computing device 20 compares the reference response at the sensing elements 14 with the computed response for a determined set of excitations and admittivity distribution. In one embodiment, the computing device 20 searches for a set of admittivity distribution that minimizes a difference according to equation 7:

$$\min\{\|U_m - U_E(\sigma)\|^2 + \alpha \|P\sigma\|^2\}, \quad \text{equation 7}$$

wherein "P" is a regularization matrix, "α" is a conditioning parameter, and α>0. "$U_m$" is the measured potential and "$U_E$" is the computed response or computed potential. In one embodiment, equation 7 is solved by Gauss Newton's method iteratively. In each iteration, the computing device 20 computes a correction ($\Delta\rho_i$) for the impedivity ($\rho_i$) according to equation 8 below:

$$\Delta\rho_i = (J^T J + \alpha P^T P)^{-1}(J^T(U_m - U_{fwd}(\rho_i)) - \alpha P^T P \rho_i), \quad \text{equation 8}$$

wherein "J" is the Jacobian matrix derived by equation 6. Accordingly, each iteration of equation 8 creates a new set of impedivities of the geometry.

At block 38, in the illustrated embodiment, the computing device 20 determines if an error between the new set of conductivities and the computed conductivities is sufficiently small. If yes, the process stops; if not, the process continues at block 40.

At block 40, in certain embodiments, the computing device 20 updates at least a subset of the nodes in the geometry to form an updated mesh where the connection relationships of the nodes remains the same as the previous mesh. In other words, each element boundary of the updated mesh is defined by the same two nodes as compared in the first mesh. In certain embodiments, the number of nodes and connectivity relationships of the nodes in the updated mesh remains the same as the previous mesh. In certain embodiments, the computing device 20 updates the assumption of the geometry of the object 12 based on measured data, computed data, updates from the computing device 20, or data from other instruments.

In certain embodiments, the computer apparatus 20 identifies at least one region of interest 45, and forms the updated mesh to refine the elements 44 at the region of interest 45. In certain embodiments, an area including at least one element with a specific admittivity range may be of greater interest than other areas in the geometry, and this area is also referred to as "region of interest" hereinafter. In one embodiment, at block 40, the computing device 20 identifies at least one region of interest 45 that has a specific admittivity range, and drives the nodes of the elements nearby the region of interest 45 to move toward the region of interest 45. Accordingly, the elements at the region of interest 45 get smaller in the updated mesh, and the image obtained from the SFT method has a better spatial resolution for the region of interest 45 as being compared to the previous mesh.

Figure 5:
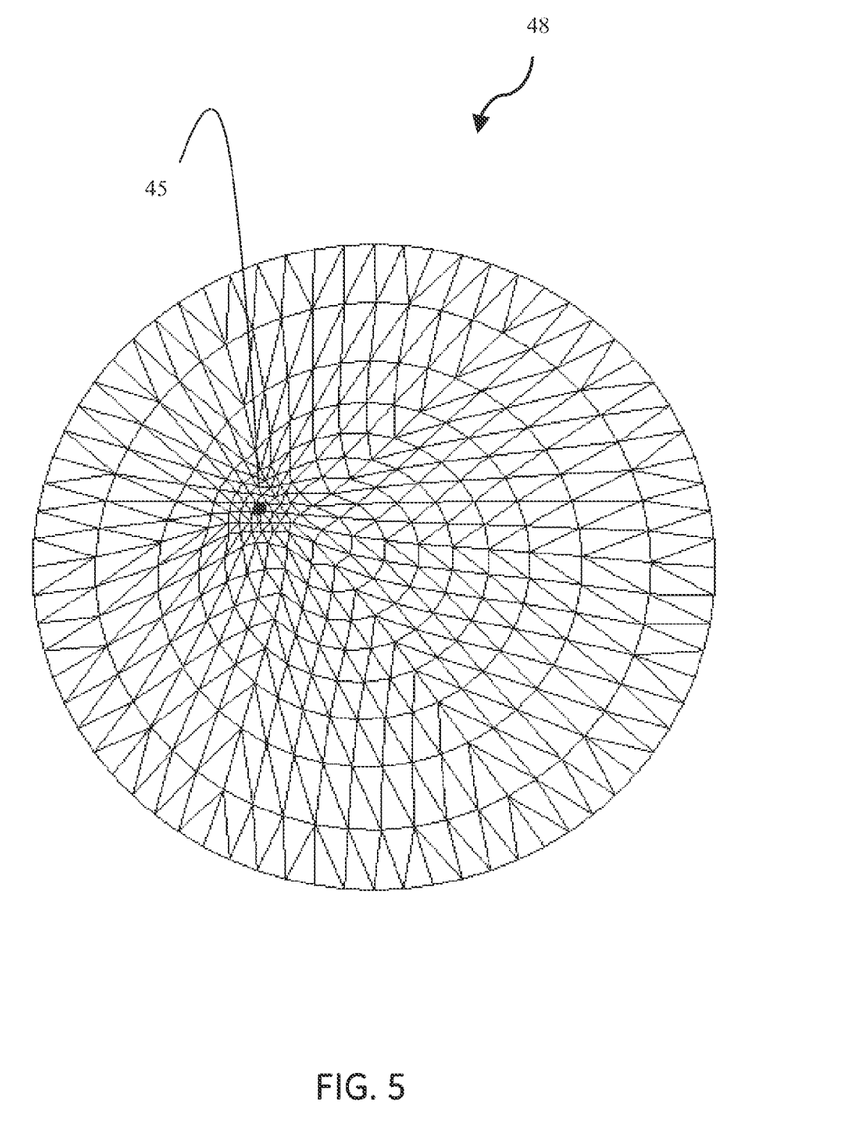
FIG. 5 illustrates an updated mesh defined in the object using the SFT method for reconstructing the object according to one embodiment.
Figure 6:
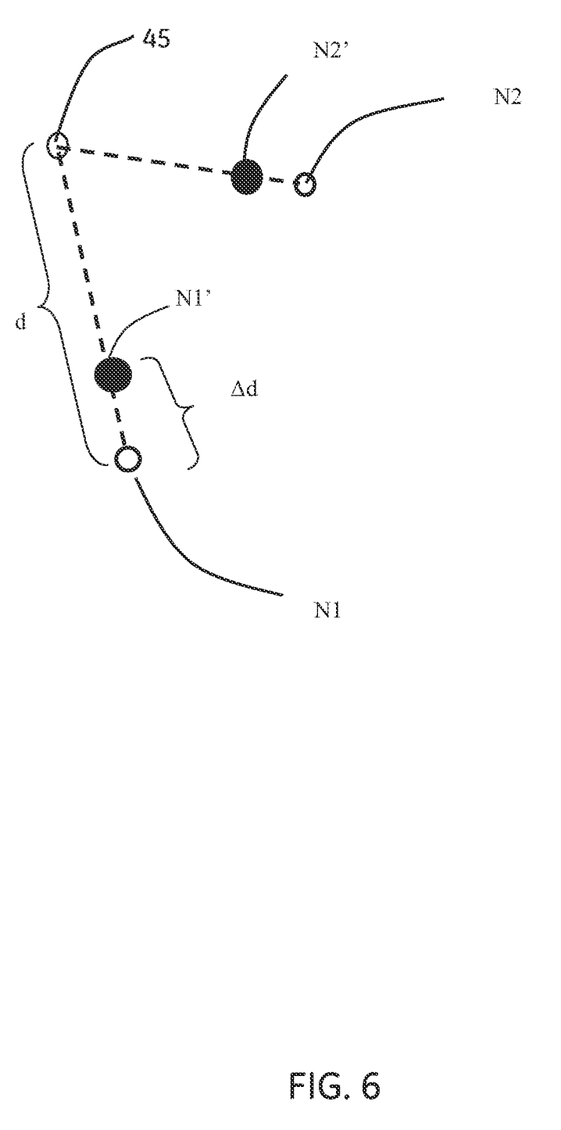
FIG. 6 illustrates movement of two exemplary nodes from a position in the first mesh of FIG. 3 to an updated position in the updated mesh in FIG. 5 according to one embodiment.

In one embodiment, each node in the first mesh 42 in FIG. 3 moves toward the region of interest 45 to form an updated mesh 48 in FIG. 5. In one embodiment, a movement distance of each node is a function of the distance between the node and a determined point, a center, or an edge of the area of interest. FIG. 6 illustrates two exemplary nodes (N1, N2) in the first mesh 42 that move to location (N1', N2') in the updated mesh 48 toward the region of interest 45. In the illustrated embodiment of FIG. 6, the movement distance (Δd) from N1 to N1' is defined as inversely proportional to the a power of the distance (d) much as the square of or cube of the distance, according to equation 9 below for example:

$$\Delta d = \frac{k}{d^2},\qquad\text{equation 9}$$

wherein "k" is a coefficient. Accordingly, the region of interest 45 has finer elements in the updated mesh 48, and the region of interest 45 in a next iteration has a higher spatial resolution and computational accuracy as compared with the previous iteration, In each iteration, the number of the elements and the correspondence relationship between the elements of the matrices and the elements of the mesh 18 remain unchanged as compared to the first mesh 42.

In certain embodiments, the movements of the nodes are not only determined by the distances between the nodes to the region of interest 45, but also by additional constraints like optimal sensitivity for a field distribution, or by physical constraints on the locations of the nodes. In one embodiment, in a SFT method, electrical current density decreases as distance between a node and the electrodes increases. A small movement distance for nodes adjacent to the electrodes may have similar effect as compared with a large movement distance for nodes far from the electrodes, Accordingly, a movement scaling parameter may be designed to compensate this constraint according to equation 10 for example:

$$\Delta d = \frac{k}{d^2}\cdot r^2\qquad\text{equation 10}$$

wherein "r" is the shortest distance of the node to any of the electrodes 14.

In certain embodiments, the movement of the nodes is subject to physical constraints defined by the geometry of the object 12, or the boundary of the region of interest 45. The nodes that define the locations and the size of the sensing elements have to be in alignment with the boundaries of the sensing elements. The nodes that are on the boundaries of the object 12 shall be constrained to the boundaries during updating of the mesh. In certain embodiments, there are empty regions in the object 12 that should not include any node, and the movement of the nodes shall be constrained to prevent nodes from moving into the empty regions.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An iterative method for computing a distribution of one or more properties within an object, the method comprising:
    defining a first mesh of the object, the first mesh including a plurality of nodes and elements;
    applying an excitation to the object;
    computing a response of the object to the applied excitation;
    obtaining a reference response of the object corresponding to the applied excitation;
    computing a distribution of one or more properties of the object using the computed response, the reference response, and the first mesh; and
    updating at least a subset of the nodes of the first mesh to form an updated mesh of the object by moving each node of the subset of the first mesh towards the region of interest using a movement scaling parameter as defined by, $$\Delta d = \frac{k}{d^2}\times r^2,$$

wherein Δd is a movement distance for each node, d is a distance between the region of interest and a current location for each node, k is a coefficient, and r is the shortest distance of the node to any of the plurality of sensing elements, and
   wherein a connectivity relationship between each of the subset of the nodes in the updated mesh remains the same as in the first mesh.

2. The method of claim 1, wherein computing the response of the object to the applied excitation comprises using the first mesh or a second mesh and the applied excitation.

3. The method of claim 1, wherein computing the response of the object to the applied excitation comprises using the applied excitation and an analytic model.

4. The method of claim 1, wherein the excitation includes one or more of electrical signals, optical signals, thermal sources, mechanical excitations, acoustic signals, and magnetic field, and wherein the reference response includes one or more electrical signals, optical signals, thermal responses, mechanical responses, acoustic responses, and magnetic field responses corresponding in type to the excitation.

5. The method of claim 4, wherein applying the excitation to the object comprises applying the excitation via a plurality of sensing elements coupled to the object, and wherein computing the response of the object comprises computing the response for each of the plurality of sensing elements.

6. The method of claim 1, wherein obtaining the reference response of the object to the applied excitation comprises measuring a response on a plurality of sensing elements configured to couple to the object.

7. The method of claim 1, wherein obtaining the reference response comprises obtaining a reference signal by simulation or analytic derivation from a reference database.

8. The method of claim 1, wherein defining the first mesh of the object comprises defining a two-dimensional mesh including a plurality of two dimensional elements or defining a three-dimensional mesh including a plurality of three-dimensional elements.

9. The method of claim 1, wherein the movement distance of each node is inversely proportional to the power of the distance from each node to a determined point of the region of interest or to an edge of the region of the interest.

10. The method of claim 1, wherein moving each of the nodes in the subset is restricted according to a determined constraint.

11. The method of claim 1, further comprising:
applying an updated excitation on the object;
computing an updated response of the object to the updated excitation; and
computing an updated distribution of the one or more properties of the object using the updated computed response.

12. The method of claim 11, wherein applying the updated excitation to the object comprises applying the same excitation or applying a different excitation to the object as compared to the excitation applied to the object before the first mesh is updated.

13. A soft field tomography system comprising:
a plurality of sensing elements configured to couple to an object;
an excitation driver coupled to the plurality of sensing elements for transmitting an excitation to the plurality of sensing elements; and
a computing device coupled to the excitation driver, the computing device being configured to:
define a first mesh of the object, the first mesh including a plurality of nodes and elements;
compute a response of the object according to the applied excitation;
obtain a reference response to the applied excitation;
compute a distribution of one or more properties of the object using the computed response, the reference response, and the first mesh;
identify a region of interest according to the computed distribution of the one or more properties of the object; and
update at least a subset of the nodes in the first mesh to generate an updated mesh of the object by moving each node of the subset of the first mesh towards the region of interest using a movement scaling parameter as defined by, $$\Delta d = \frac{k}{d^2} \times r^2,$$

wherein $\Delta d$ is a movement distance for each node, d is a distance between the region of interest and a current location for each node, k is a coefficient, and r is the shortest distance of the node to any of the plurality of sensing elements, and wherein a connectivity relationship between each of the subset of the nodes in the updated mesh remains the same as in the first mesh.

14. The system of claim 13, further comprising a response detector coupled to the plurality of sensing elements for measurement of the reference response in response to the excitation and for transmitting the reference response to the computing device.

15. The system of claim 13, wherein the computing device is configured to calculate a movement distance of each node in the subset, and wherein the movement distance is inversely proportional to a power of a distance between each node and the region of interest.

16. The system of claim 13, wherein the computing device is configured to compute an updated distribution of one or more properties of the object on the updated mesh and to generate an image according to the updated distribution of one or more properties of the object, and wherein the system further comprises a screen to display the image.

17. A non-transitory computer readable medium comprising instructions which when executed by a processor or computer perform an iterative method of:
defining a first mesh of an object, the first mesh including a plurality of nodes and elements;
applying an excitation to the object;
computing a response of the object to the applied excitation;
obtaining a reference response of the object corresponding to the applied excitation;
computing a distribution of one or more properties of the object using the computed response, the reference response, and the first mesh; and
updating at least a subset of the nodes in the first mesh to form an updated mesh of the object by moving each node of the subset of the first mesh towards the region of interest using a movement scaling parameter as defined by, $$\Delta d = \frac{k}{d^2} \times r^2,$$

wherein $\Delta d$ is a movement distance for each node, d is a distance between the region of interest and a current location for each node, k is a coefficient, and r is the shortest distance of the node to any of the plurality of sensing elements, and wherein a connectivity relationship between each of the subset of the nodes in the updated mesh remains the same as in the first mesh.

* * * * *